US012472084B2

(12) United States Patent
Kitay et al.

(10) Patent No.: US 12,472,084 B2
(45) Date of Patent: Nov. 18, 2025

(54) HAND IMMOBILIZER

(71) Applicants: Garry Kitay, Jacksonville, FL (US); Instrument Specialists, Inc., Boerne, TX (US)

(72) Inventors: Garry Kitay, Jacksonville, FL (US); Casey Shepherd, Boerne, TX (US); Chris Harrelson, Boerne, TX (US)

( * ) Notice: Subject to any disclaimer, the term of this patent is extended or adjusted under 35 U.S.C. 154(b) by 222 days.

(21) Appl. No.: 18/451,784

(22) Filed: Aug. 17, 2023

(65) Prior Publication Data

US 2024/0058154 A1 Feb. 22, 2024

Related U.S. Application Data

(60) Provisional application No. 63/399,026, filed on Aug. 18, 2022.

(51) Int. Cl.
*A61F 5/058* (2006.01)

(52) U.S. Cl.
CPC ................................ *A61F 5/05875* (2013.01)

(58) Field of Classification Search
CPC ................ A61F 5/05875; A61F 5/3761; A61F 5/05858; A61F 5/05841; A61F 5/058; A61F 5/05; A61F 5/04; A61F 5/01; A61F 5/00; A61F 5/37
See application file for complete search history.

(56) References Cited

U.S. PATENT DOCUMENTS

| | | | | |
|---|---|---|---|---|
| 4,781,178 | A | 11/1988 | Gordon | |
| 5,560,375 | A * | 10/1996 | Kabanek | A61F 5/3761 128/878 |
| 5,855,209 | A * | 1/1999 | Hernandez | A61F 5/3761 128/878 |
| 2015/0068534 | A1* | 3/2015 | Lubbers | A61F 5/3761 128/845 |
| 2021/0267786 | A1* | 9/2021 | Kitay | A61F 5/3761 |
| 2021/0307950 | A1 | 10/2021 | Perelman et al. | |

OTHER PUBLICATIONS

McKesson, Surgical Hand Immobilizer Framer Malleable Lead Left or Right Hand Gray Standard, https://mms.mckesson.com/product/634461/Miltex-PM-4480 (accessed May 2020).

* cited by examiner

*Primary Examiner* — Tarla R Patel
(74) *Attorney, Agent, or Firm* — Werner IP Law, P.C.

(57) ABSTRACT

A hand immobilizer which has a body in the general shape of the hand, including a portion shaped like the metacarpus and wrist of the hand and distally extending portions or digits shaped like the fingers of the hand. At least some of the digits of the hand immobilizer comprise first and second laterally spaced tines or prongs.

16 Claims, 3 Drawing Sheets

HAND IMMOBILIZER

CROSS REFERENCE TO RELATED APPLICATION

This application claims priority to U.S. Application No. 63/399,026 filed on Aug. 18, 2022, the disclosure of which is incorporated herein by reference for all purposes.

FIELD OF THE INVENTION

The present invention relates to hand immobilizers used in surgical or other settings.

BACKGROUND OF THE INVENTION

Hand immobilizers used during surgery either on the hand or some other part of the body are disclosed for example in U.S. Pat. Nos. 5,560,375 and 5,855,209 (collectively Hand Immobilizer Patents), and patent application US 2021/0267786A1, all of which are incorporated herein by reference for all purposes.

As can be seen from the Hand Immobilizer Patents, the hand immobilizers do not have digit, e.g., finger, restraints other than on the ends of the digits, those restraints being bendable, as shown in the Hand Immobilizer Patents, over the tips of the patient's finger. However, there are instances wherein a digit restraint which could be more selectively positioned on a digit would be desirable, e.g., to better isolate or immobilize the digit.

SUMMARY OF THE INVENTION

In one aspect, the present invention relates to a hand immobilizer wherein a finger(s) of the hand can be gripped more securely.

In another aspect, the present invention relates to a hand immobilizer wherein the digits of the hand immobilizer are configured to allow each finger of a hand to be gripped in a variety of ways, e.g., to permit exposure of each portion of the finger.

These and further features and advantages of the present invention will become apparent from the following detailed description, wherein reference is made to the figures in the accompanying drawings.

DETAILED DESCRIPTION OF PREFERRED EMBODIMENTS

As used herein the term "finger" is generally intended to be inclusive of the thumb. If the thumb is specifically meant, it will be so identified separately.

Figure 1:
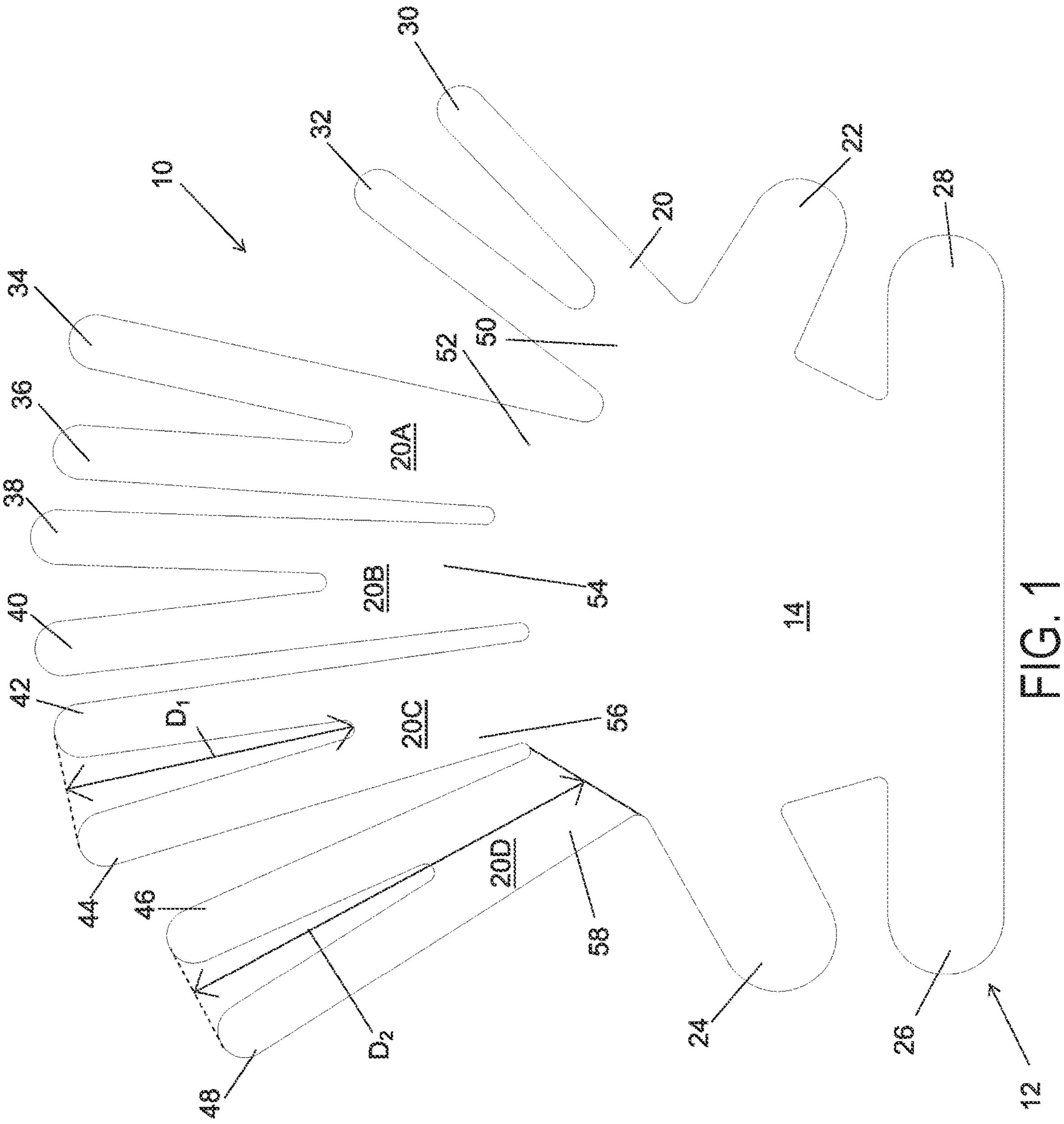
FIG. 1 is a plan view of one embodiment of the hand immobilizer of the present invention.

Referring first to FIG. 1, there is shown one embodiment of the hand immobilizer (HI).

The HI, shown generally as 10, comprises a plate like body 12 having a front face/side and a back face/side. Body 12 comprises a main portion 14 generally corresponding to the metacarpus and wrist of a human hand. Extending distally or outwardly from the main portion 14 are digits 20-20D corresponding to the respective shapes of the fingers of a hand. As can be seen, the digits 20-20D are splayed outwardly from main body portion 14 so as to conform to the shape of a human hand when the fingers are spread. Also extending laterally outwardly from body portion 14 are tabs 22, 24, 26, and 28.

As can be seen from FIG. 1, each of the digits 20-20D is comprised of first and second longitudinally extending spaced prongs or tines 30, 32, 34, 36, 38, 40, 42, 44, 46, and 48, each of the prongs having a rounded tip. As can be seen, each pair of the prongs or tines form a generally V-shaped valley therebetween. Each of the digits 20-20D has a base portion at the juncture of main body portion 14. Thus, digit 20 has a base 50, digit 20A has a base 52, digit 20B has a base 54, digit 20C has a base 56, and digit 20D has a base 58. In general, the base portions 50-58 are at the juncture between the respective digits and the main body 14. In general, as to each digit, the depth ($D_1$) of the valley between the prongs shown by example with respect to digit 20C is from about 40% to about 80% of the length ($D_2$) of the digit as measured from a line tangential to the tips of the paired prongs to the base, i.e., generally the juncture between the digit and the body 14, as shown for example with respect to digit 20D. In a preferred embodiment, digit 20 is smaller in length to accommodate a patient's thumb.

As shown, each of the digits of the "split finger" design shows the respective, paired tines of a given digit laterally spaced from one another by the valley therebetween. It is to be understood that lateral spacing between the tines can vary but should be sufficient to permit some degree of overlap of the paired tines. Further, the spacing of the tines allows each of the tines to more easily accommodate being bent over a patient's finger at more than one location if desired.

The HI 10 can be constructed of various materials in accordance with the teachings of the Hand Immobilizer Patents. Thus, as taught in those patents, aluminum is one preferred material that can be employed. However, the HI 10 could also be made of lead or other pliable/deformable materials, including certain composites. As noted, the HI is generally a platelike structure preferably having first and second planar faces or sides, the thickness of the platelike structure being from about 0.025" to about 0.05". In general, the thickness of the plate-like structure forming the HI of the present invention should be thin enough such that the prongs/tines can be easily deformed around the respective finger(s) of the hand of a patient, but yet be thick enough to maintain such a deformed position and to maintain a generally planar shape until sufficient force is used to bend the various tines and/or the tabs. Preferably the thickness of the structure is sufficient that the above goals are achieved while minimizing the amount of material, thus minimizing waste if the HI is to be disposable.

As taught in U.S. Pat. No. 5,855,209 ('209 Patent), one of the Hand Immobilizer Patents, one or both faces of the HI of the present invention can have an overlay or laminate of a cushioning material which can be a sponge-like material or other plastic material which supplies some moderate degree of cushioning to the patient's hand when being held by the HI 10 of the present invention. The cushioning layer, either as to one face or both faces, can have a thickness ranging from about an ⅛" to about ⅜". It will be appreciated that cushioning is optional.

As explained in the Hand Immobilizer Patents, the tabs 22, 24, 26 and 28 are useful in maintaining the relative position of the patient's hand to the HI when the patient's hand is immobilized. Thus the tabs can be wrapped around the wrist and/or metacarpus of the patient as needed and restrain the HI from sliding movement relative to the hand of the patient and thus provide overall stability to the immobilized hand of the patient when the HI is in use.

Figure 2:
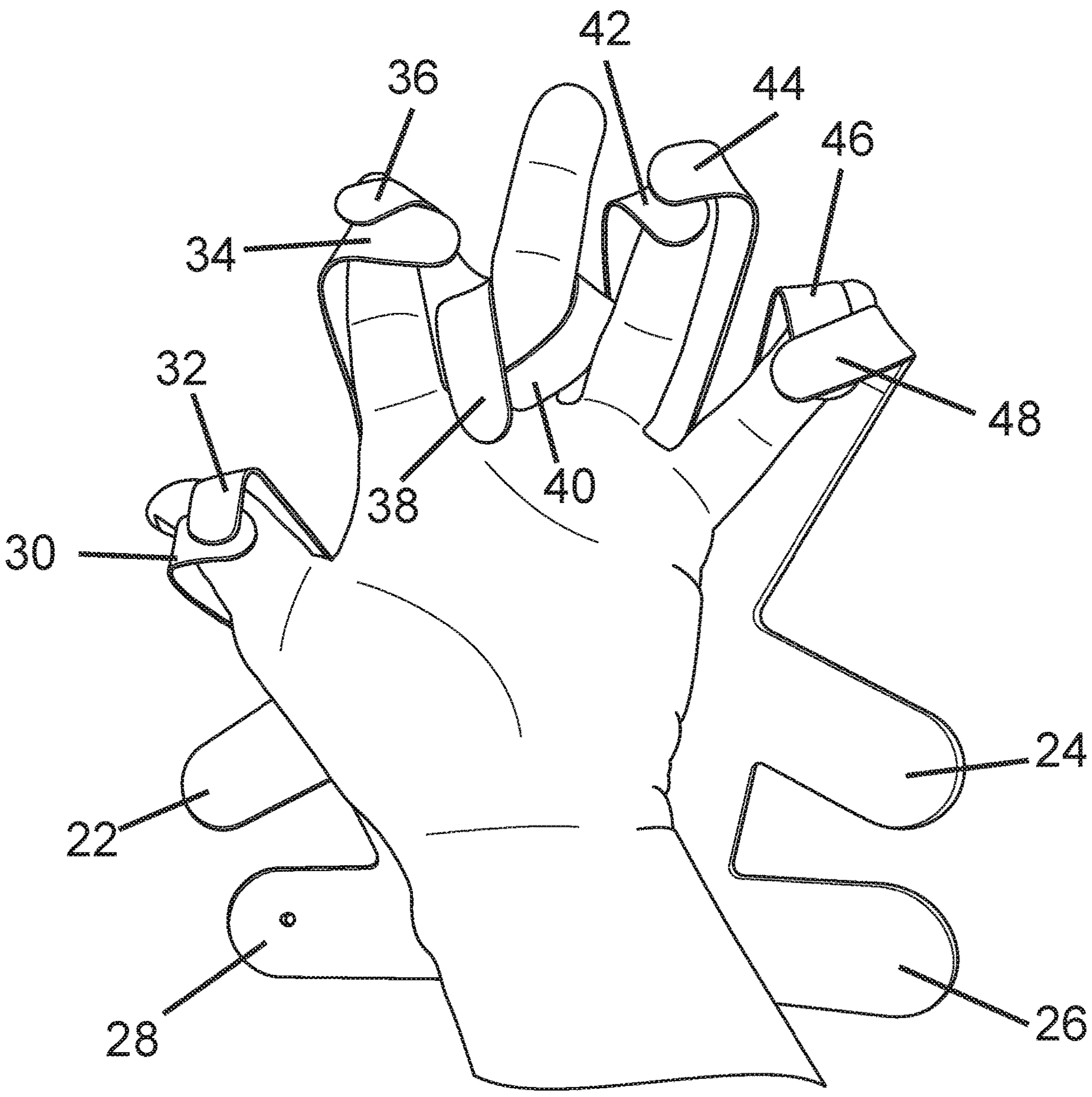
FIG. 2 is a photo showing how each finger/thumb of a hand can be gripped and such that a middle finger of a hand can be grasped in such a way that the distal portion thereof is accessible for surgery.
Figure 3:
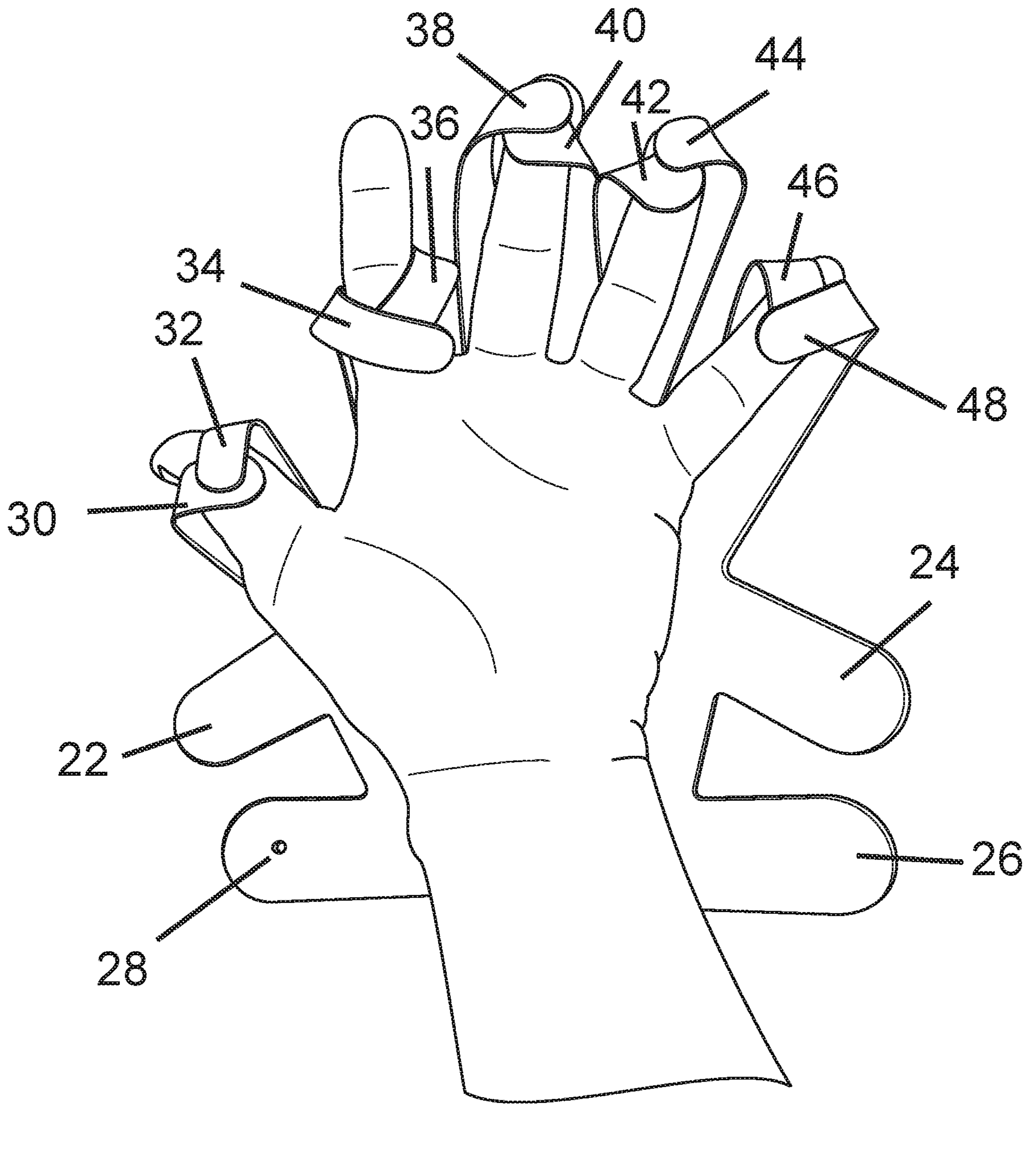
FIG. 3 is a photo similar to FIG. 2 but showing how the index finger can be grasped while permitting free access to the distal portion thereof.

It will be appreciated that the HI of the present invention is ambidextrous in the sense that it can be used on either the left or the right hand simply by flipping it from one face to the other. This is also shown in that FIG. 1 shows the HI for use with a right hand, while FIGS. 2 and 3 depict use of the HI with a left hand. It will also be understood that if a cushioning is employed, to maintain the ambidexterity of the HI, the cushioning could be placed on both faces. Obviously, the Hi's could be made with padding or cushioning on a single face e.g., either a right-handed or left-handed structure.

The versatility of the HI of the present invention can be seen with reference to FIGS. 2 and 3 which are photos of the left hand of a person being immobilized by the HI of the present invention and shows how the "split finger" design employing the two tines or prongs can be used to grasp a desired finger in various ways. For example, with reference to FIG. 2 the middle finger can be grasped at the base of the digit, thereby allowing surgical access to the distal portion of the middle finger.

Similarly, with reference to FIG. 3, it can be seen how the index finger can be grasped in such a way that the tip portion thereof is readily accessible.

The HI can be easily made by metal stamping, laser cutting or other such techniques that do not require any expensive machining and can be made in various sizes to accommodate pediatric and adult patients.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A hand immobilizer comprising:

a body in the general shape of a human hand, said body having a portion shaped to a metacarpus and wrist of said human hand shape and at least one outwardly extending digit shaped to a finger of said human hand shape, said digit comprising first and second elongate prongs;

wherein said first and second elongate prongs are separated by a V-shaped valley therebetween, the depth of said valley being from about 40% to about 80% of the length of said digit as measured from a line tangential to the tips of the prongs to the juncture between the digit and the body.

2. The hand immobilizer of claim 1, wherein said hand immobilizer is made of a pliable material.

3. The hand immobilizer of claim 2, wherein said pliable material comprises aluminum or lead.

4. The hand immobilizer of claim 1, wherein said hand immobilizer has a thickness of from about 0.025 inches to about 0.05 inches.

5. The hand immobilizer of claim 1, further comprising an overlay of cushioning material.

6. The hand immobilizer of claim 5, wherein said overlay of cushioning material has a thickness of from about 0.125 inches to about 0.375 inches.

7. The hand immobilizer of claim 1, further comprising at least one tab extending from said body.

8. The hand immobilizer of claim 1, further comprising a plurality of tabs extending from said body.

9. A hand immobilizer comprising:

a body in the general shape of a human hand, said body having a portion shaped to a metacarpus and wrist of said human hand shape and a plurality of outwardly extending digits shaped to respective fingers of said human hand shape, each of said digits comprising respective first and second elongate prongs;

wherein each of said first and second elongate prongs of each of said digits are separated by a V-shaped valley therebetween, the depth of said valley being from about 40% to about 80% of the length of said respective digit as measured from a line tangential to the tips of the prongs to the juncture between said respective digit and the body.

10. The hand immobilizer of claim 9, wherein said hand immobilizer is made of a pliable material.

11. The hand immobilizer of claim 10, wherein said pliable material comprises aluminum or lead.

12. The hand immobilizer of claim 9, wherein said hand immobilizer has a thickness of from about 0.025 inches to about 0.05 inches.

13. The hand immobilizer of claim 9, further comprising an overlay of cushioning material.

14. The hand immobilizer of claim 13, wherein said overlay of cushioning material has a thickness of from about 0.125 inches to about 0.375 inches.

15. The hand immobilizer of claim 9, further comprising at least one tab extending from said body.

16. The hand immobilizer of claim 9, further comprising a plurality of tabs extending from said body.

* * * * *